(12) United States Patent
Möckel et al.

(10) Patent No.: US 7,074,607 B2
(45) Date of Patent: Jul. 11, 2006

(54) POLYNUCLEOTIDE SEQUENCES WHICH ENCODE THE ZWA1 GENE

(75) Inventors: Bettina Möckel, Düsseldorf (DE); Walter Pfefferle, Halle (DE); Achim Marx, Bielefeld (DE); Jörn Kalinowski, Bielefeld (DE); Brigitte Bathe, Salzkotten (DE); Alfred Pühler, Bielefeld (DE)

(73) Assignee: Degussa AG, Dusseldorf (DE)

( * ) Notice: Subject to any disclaimer, the term of this patent is extended or adjusted under 35 U.S.C. 154(b) by 217 days.

(21) Appl. No.: 10/640,263

(22) Filed: Aug. 14, 2003

(65) Prior Publication Data

US 2004/0063180 A1    Apr. 1, 2004

Related U.S. Application Data

(62) Division of application No. 09/731,909, filed on Dec. 8, 2000, now Pat. No. 6,632,644.

(30) Foreign Application Priority Data

Dec. 9, 1999 (DE) ................................. 199 59 328

(51) Int. Cl.
*C12P 1/00* (2006.01)
*C12N 1/20* (2006.01)
*C12N 15/00* (2006.01)
*C07K 1/00* (2006.01)
*C07H 21/02* (2006.01)

(52) U.S. Cl. ............ 435/252.3; 435/41; 435/106; 435/115; 435/252.3; 435/320.1; 530/350; 536/23.1

(58) Field of Classification Search ............ 435/41, 435/106, 115, 252.3, 320.1; 530/350; 536/23.1
See application file for complete search history.

(56) References Cited

U.S. PATENT DOCUMENTS 5,643,758 A * 7/1997 Guan et al. ............... 435/69.7

FOREIGN PATENT DOCUMENTS

EP     0 435 132 B1    7/1991
WO   WO 01/04325 A1    1/2001

OTHER PUBLICATIONS

Mita et al. Accession AU003526. Jan. 19, 1999.*
Reinhard Kramer, "Genetic and Physiological approaches for the production of amino acids," Journal of Biotechnology 45 (1996), pp. 1-21.

* cited by examiner

*Primary Examiner*—Tekchand Saidha
*Assistant Examiner*—Christian L. Fronda
(74) *Attorney, Agent, or Firm*—Smith, Gambrell & Russell, LLP

(57) ABSTRACT

The invention relates to an isolated polynucleotide comprising a polynucleotide sequence chosen from the group consisting of
a) polynucleotide which is identical to the extent of at least 70% to a polynucleotide which codes for a polypeptide which comprises the amino acid sequence of SEQ ID NO 2,
b) polynucleotide which codes for a polypeptide which comprises an amino acid sequence which is identical to the extent of at least 70% to the amino acid sequence of SEQ ID NO 2
c) polynucleotide which is complementary to the polynucleotides of a) and b) and
d) polynucleotide comprising at least 15 successive nucleotides of the polynucleotide sequence of a), b) or c),
and processes for the fermentative preparation of L-amino acid with amplification of the zwa1 gene in the coryneform bacteria employed.

18 Claims, 1 Drawing Sheet

Figure 1: Plasmid map of pCR2.1zwa1exp
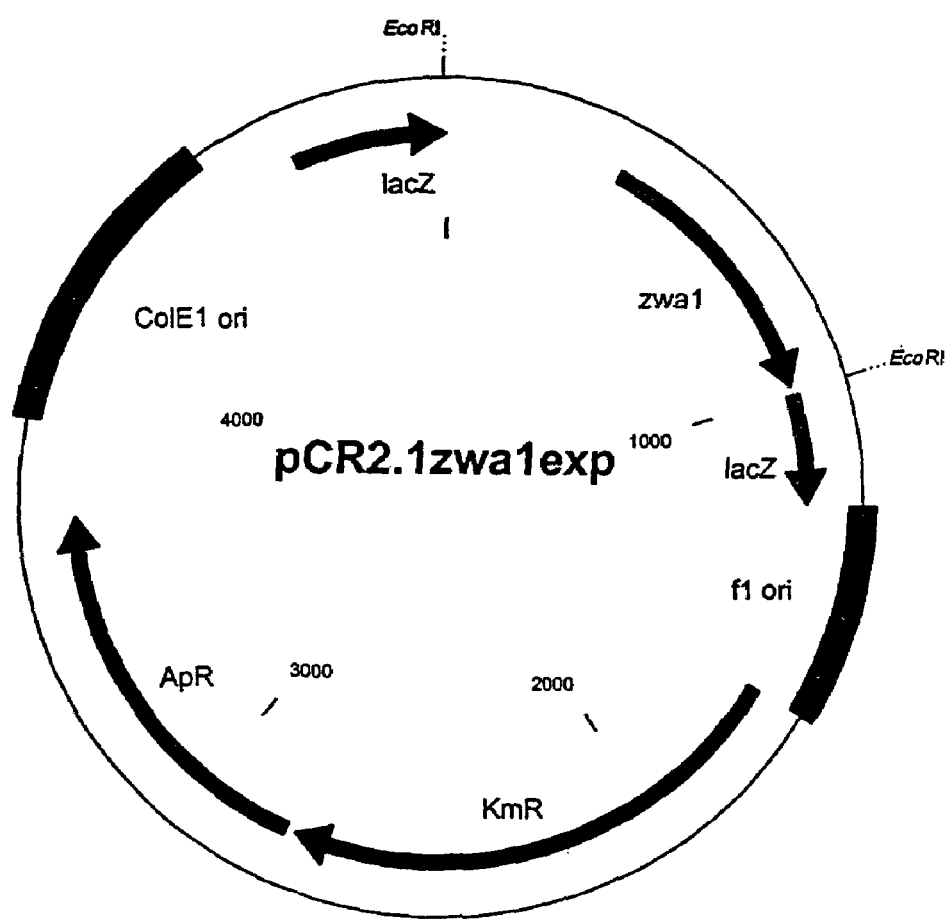

SEQUENCE LISTING

<160> NUMBER OF SEQ ID NOS: 4

<210> SEQ ID NO 1
<211> LENGTH: 1260
<212> TYPE: DNA
<213> ORGANISM: Corynebacterium glutamicum
<220> FEATURE:
<221> NAME/KEY: -10_signal
<222> LOCATION: (383)..(388)
<223> OTHER INFORMATION:
<220> FEATURE:
<221> NAME/KEY: -35_signal
<222> LOCATION: (360)..(365)
<223> OTHER INFORMATION:
<220> FEATURE:
<221> NAME/KEY: CDS
<222> LOCATION: (413)..(1009)
<223> OTHER INFORMATION:

<400> SEQUENCE: 1

```
ccgaaatatt ccaaatatgt aacataaatc acacccgatg attcaggcgg gatgacctgc      60
gacttcaagg tcgcaccaaa gtcagattga tatagatttc gtaaataacg tgacacaatc     120
gtgaccttcg ggttaccgtg tatcccaggc accgcaacag ttcatctgca agtccggctc     180
atcgccaaac cctgtctggg gtcggaagtt gaacaacctc cttggtgcaa cagaacttta     240
aaccacaaac tcccgcattc atgtgggcca tattgcagac agggacgggg aaaccaccca     300
ccatcttttc acaaaagaag gcatggaggc caactccttg gggtgaagcc agacatccac     360
tggcagagca actcctccgc tctaaccccga cagctaacct cgacggcgac aa atg aga    418
                                                               Met Arg
                                                                 1
```

```
gga aaa ctt ttc atg gga cgt cac tcc act aag act agc tcc gcg ttc      466
Gly Lys Leu Phe Met Gly Arg His Ser Thr Lys Thr Ser Ser Ala Phe
      5                  10                  15 acc aag ctc gca gct tcc acc atc gct ttc ggt gct gct gca acc atc      514
Thr Lys Leu Ala Ala Ser Thr Ile Ala Phe Gly Ala Ala Ala Thr Ile
 20                  25                  30 atg gct cct tct gca tct gct gca cct gat tcc gac tgg gat cgc ctc      562
Met Ala Pro Ser Ala Ser Ala Ala Pro Asp Ser Asp Trp Asp Arg Leu
 35                  40                  45                  50 gca cag tgc gag tcc ggt ggt aac tgg gca atc aac acc ggt aac ggc      610
Ala Gln Cys Glu Ser Gly Gly Asn Trp Ala Ile Asn Thr Gly Asn Gly
                 55                  60                  65 tac cac ggt ggt ctg cag ttc tcc gct agc acc tgg gct gct tac ggc      658
Tyr His Gly Gly Leu Gln Phe Ser Ala Ser Thr Trp Ala Ala Tyr Gly
             70                  75                  80 ggc cag gag ttc gct acc tac gca tac cag gca acc cgt gag cag cag      706
Gly Gln Glu Phe Ala Thr Tyr Ala Tyr Gln Ala Thr Arg Glu Gln Gln
         85                  90                  95 atc gct gtt gca gag cgc acc ttg gct ggt cag ggc tgg ggc gca tgg      754
Ile Ala Val Ala Glu Arg Thr Leu Ala Gly Gln Gly Trp Gly Ala Trp
    100                 105                 110 cct gct tgc tcc gct tcc ctt gga ctg aac tcc gct cca acc cag cgt      802
Pro Ala Cys Ser Ala Ser Leu Gly Leu Asn Ser Ala Pro Thr Gln Arg
115                 120                 125                 130 gac ctc tcc gct acc acc tcc acc cca gag cca gct gca gct gca cca      850
Asp Leu Ser Ala Thr Thr Ser Thr Pro Glu Pro Ala Ala Ala Ala Pro
                135                 140                 145 gct gtt gct gag tac aac gct cct gca gcc aac atc gca gtt ggc tcc      898
Ala Val Ala Glu Tyr Asn Ala Pro Ala Ala Asn Ile Ala Val Gly Ser
            150                 155                 160
```

```
acc gac ttg aac acc atc aag tcc acc tac ggc gct gtc acc ggc acc       946
Thr Asp Leu Asn Thr Ile Lys Ser Thr Tyr Gly Ala Val Thr Gly Thr
        165                 170                 175 ctc gct cag tac ggc atc acc gtt cca gct gag gtt gag tct tac tac       994
Leu Ala Gln Tyr Gly Ile Thr Val Pro Ala Glu Val Glu Ser Tyr Tyr
        180                 185                 190 aac gct ttc gtc ggc taaatctagc tgcactttt aaaagggagg gaaccttaaa       1049
Asn Ala Phe Val Gly
195 cgggttccct ccctttttgc atgccatttc acgacgcgcc agtcatcctt ttgtgaattg     1109 ggcaccaaga tttcctgatt ttggccacca ttttgccgaa accttggtgc cgaaagtacg     1169 cccagtagaa aaaccgcatg aaaaaagagg caacaccgcc gaaacgggtt gcctcttttt     1229 taagtttctt agcggttgat ccgggtgtac g                                    1260

<210> SEQ ID NO 2
<211> LENGTH: 199
<212> TYPE: PRT
<213> ORGANISM: Corynebacterium glutamicum

<400> SEQUENCE: 2

Met Arg Gly Lys Leu Phe Met Gly Arg His Ser Thr Lys Thr Ser Ser
1               5                   10                  15

Ala Phe Thr Lys Leu Ala Ala Ser Thr Ile Ala Phe Gly Ala Ala Ala
                20                  25                  30

Thr Ile Met Ala Pro Ser Ala Ser Ala Ala Pro Asp Ser Asp Trp Asp
            35                  40                  45

Arg Leu Ala Gln Cys Glu Ser Gly Gly Asn Trp Ala Ile Asn Thr Gly
        50                  55                  60

Asn Gly Tyr His Gly Gly Leu Gln Phe Ser Ala Ser Thr Trp Ala Ala
65                  70                  75                  80

Tyr Gly Gly Gln Glu Phe Ala Thr Tyr Ala Tyr Gln Ala Thr Arg Glu
                85                  90                  95

Gln Gln Ile Ala Val Ala Glu Arg Thr Leu Ala Gly Gln Gly Trp Gly
            100                 105                 110

Ala Trp Pro Ala Cys Ser Ala Ser Leu Gly Leu Asn Ser Ala Pro Thr
        115                 120                 125

Gln Arg Asp Leu Ser Ala Thr Thr Ser Thr Pro Glu Pro Ala Ala Ala
130                 135                 140

Ala Pro Ala Val Ala Glu Tyr Asn Ala Pro Ala Ala Asn Ile Ala Val
145                 150                 155                 160

Gly Ser Thr Asp Leu Asn Thr Ile Lys Ser Thr Tyr Gly Ala Val Thr
                165                 170                 175

Gly Thr Leu Ala Gln Tyr Gly Ile Thr Val Pro Ala Glu Val Glu Ser
            180                 185                 190

Tyr Tyr Asn Ala Phe Val Gly
        195

<210> SEQ ID NO 3
<211> LENGTH: 19
<212> TYPE: DNA
<213> ORGANISM: Corynebacterium glutamicum

<400> SEQUENCE: 3
tcacaccgat gattcaggc                                                    19
```

-continued

```
<210> SEQ ID NO 4
<211> LENGTH: 20
<212> TYPE: DNA
<213> ORGANISM: Corynebacterium glutamicum

<400> SEQUENCE: 4
agatttagcc gacgaaagcg                                            20
```

US 7,074,607 B2

POLYNUCLEOTIDE SEQUENCES WHICH ENCODE THE ZWA1 GENE

CROSS REFERENCE TO RELATED APPLICATION

This application is a division of Ser. No. 09/731,909, filed Dec. 8, 2000, now U.S. Pat. No. 6,632,644 and which is being incorporated in its entirety herein by reference.

INTRODUCTION AND BACKGROUND

The invention provides nucleotide sequences, which code for the zwa1 gene and processes for the fermentative preparation of amino acids, in particular L-lysine, using coryneform bacteria in which the zwa1 gene is amplified. All references cited herein are expressly incorporated by reference. Incorporation by reference is also designated by the term "I.B.R." following any citation.

PRIOR ART

Amino acids, in particular L-lysine, are used in human medicine and in the pharmaceuticals industry, but in particular in animal nutrition. It is known that amino acids are prepared by fermentation from strains of coryneform bacteria, in particular *Corynebacterium glutamicum*. Because of their great importance, work is constantly being undertaken to improve the preparation processes. Improvements to the processes can relate to fermentation measures, such as e.g. stirring and supply of oxygen, or the composition of the nutrient media, such as e.g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the lysine analogue S-(2-aminoethyl)-cysteine, or are auxotrophic for metabolites of regulatory importance and produce L-amino acids are obtained in this manner.

Recombinant DNA techniques have also been employed for some years for improving the strain of Corynebacterium strains which produce amino acids, by amplifying individual amino acid biosynthesis genes and investigating the effect on the amino acid production.

Review articles in this context are to be found, inter alia, in Kinoshita ("Glutamic Acid Bacteria", in: Biology of Industrial Microorganisms, Demain and Solomon (Eds.) I.B.R., Benjamin Cummings, London, UK, 1985, 115–142), Hilliger (BioTec 2, 40–44 (1991)) I.B.R., Eggeling (Amino Acids 6:261–272 (1994)) I.B.R., Jetten and Sinskey (Critical Reviews in Biotechnology 15, 73–103 (1995)) I.B.R. and Sahm et al. (Annuals of the New York Academy of Science 782, 25–39 (1996)) I.B.R.

OBJECT OF THE INVENTION

An object of the invention is to provide new measures for improved fermentative preparation of amino acids, in particular L-lysine. Amino acids, in particular L-lysine, are used in human medicine, in the pharmaceuticals industry and in animal nutrition. There is therefore a general interest in providing new improved processes for the preparation of amino acids, in particular L-lysine. When L-lysine or lysine are mentioned in the following, not only the base but also the salts, such as e.g. lysine monohydrochloride or lysine sulfate, are also meant by this.

SUMMARY OF THE INVENTION

The new DNA sequence of *C. glutamicum* which codes for the zwa1 gene and which as a constituent of the present invention is SEQ ID NO 1 and related sequences. The amino acid sequence of the corresponding gene product of the zwa1 gene has furthermore been derived from the present DNA sequence. The resulting amino acid sequence of the zwa1 gene product is SEQ ID NO 2 and related sequences.

BRIEF DESCRIPTION OF THE DRAWINGS

FIG. 1: Map of the plasmid pCR2.1zwa1exp The length data are to be understood as approximate values.

DETAILED DESCRIPTION OF THE INVENTION

The invention provides an isolated polynucleotide from coryneform bacteria, comprising a polynucleotide sequence chosen from the group consisting of a) polynucleotide which is identical to the extent of at least 70% to a polynucleotide which codes for a polypeptide which comprises the amino acid sequence of SEQ ID NO 2, b) polynucleotide which codes for a polypeptide which comprises an amino acid sequence which is identical to the extent of at least 70% to the amino acid sequence of SEQ ID NO 2, c) polynucleotide which is complementary to the polynucleotides of a) or b), and d) polynucleotide comprising at least 15 successive nucleotides of the polynucleotide sequence of a), b) or c).

The invention also provides a polynucleotide according to claim 1, this preferably being a DNA which is capable of replication, comprising:

(i) the nucleotide sequence shown in SEQ ID NO 1, or (ii) at least one sequence which corresponds to sequences (i) within the range of the degeneration of the genetic code, or (iii) at least one sequence which hybridizes with sequences complementary to sequences (i) or (ii), and optionally (iv) sense mutations of neutral function in (i).

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R. Hybridization of complementary sequences can occur at varying degrees of stringency. Sambrook et al.: Molecular Cloning, A Laboratory Manual (Cold Spring Harbor Laboratory Press, 1989) I.B.R.

The invention also provides a polynucleotide, comprising the nucleotide sequences as shown in SEQ ID NO 1, wherein the polynucleotide is a preferably recombinant DNA which is capable of replication in coryneform bacteria, a polynucleotide, which codes for a polypeptide which comprises the amino acid sequence as shown in SEQ ID NO 2, a vector containing the DNA sequence of *C. glutamicum* which codes for the zwa1 gene, contained in the vector (plasmid) pCR2.1zwa1exp., deposited in *E. coli* Top10F' under number DSM 13115 and coryneform bacteria serving as the host cell, which contain the vector in which the zwa1 gene is amplified.

The invention also provides polynucleotides which substantially comprise a polynucleotide sequence, which are obtainable by screening by means of hybridization of a corresponding gene library, which comprises the complete gene with the polynucleotide sequence corresponding to SEQ ID NO 1 or parts thereof, with a probe which comprises the sequence of the said polynucleotide according to SEQ ID NO 1 or a fragment thereof, and isolation of the DNA sequence mentioned.

Polynucleotide sequences according to the invention are suitable as hybridization probes for RNA, cDNA and DNA, in order to isolate, in the full length, cDNA which code for the Zwa1 gene product and in order to isolate those cDNA or genes which have a high similarity of sequence with that of the zwa1 gene.

Polynucleotide sequences according to the invention are furthermore suitable as primers with the aid of which DNA of genes which code for the zwa1 gene can be prepared by the polymerase chain reaction (PCR). Such oligonucleotides which serve as probes or primers comprise at least 30, preferably at least 20, very particularly preferably at lease 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include polypeptides according to SEQ ID NO 2, in particular those with the biological activity of the gene product of the zwa1 gene and also those which are identical to the extent of at least 70% to the polypeptide according to SEQ ID NO 2, preferably to the extent of at least 80%, and in particular which are identical to the extent of at least 90% to 95% to the polypeptide according to SEQ ID NO 2 and have the activity mentioned.

The invention moreover provides a process for the fermentative preparation of amino acids, in particular L-lysine, using coryneform bacteria which in particular already produce the amino acid, and in which the nucleotide sequences which code for the zwa1 gene are amplified, in particular over-expressed.

The term "amplification" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms, which the present invention provides, can prepare L-lysine from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum*, are, for example, the known wild-type strains

*Corynebacterium glutamicum* ATCC13032
*Corynebacterium acetoglutamicum* ATCC15806
*Corynebacterium acetoacidophilum* ATCC13870
*Corynebacterium melassecoloa* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and L-lysine-producing mutants or strains prepared therefrom, such as, for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715

The inventors have succeeded in isolating the new zwa1 gene of *C. glutamicum* which codes for the Zwa1 gene product. To isolate the zwa1 gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) I.B.R. or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)) I.B.R. Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164) I.B.R. in the *E. coli* K-12 strain NM554 (Raleigh et al., 1988, Nucleic Acids Research 16:1563–1575) I.B.R.

Börmann et al. (Molecular Microbiology 6(3), 317–326 (1992)) I.B.R. in turn describe a gene library of *C. glutamicum* ATCC13032 using the cosmid pHC79 (Hohn and Collins, Gene 11, 291–298 (1980)) I.B.R. To prepare a gene library of *C. glutamicum* in *E. coli* it is also possible to use plasmids such as pBR322 (Bolivar, Life Sciences, 25, 807–818 (1979)) I.B.R. or pUC9 (Vieira et al., 1982, Gene, 19:259–268) I.B.R. Suitable hosts are, in particular, those *E. coli* strains, which are restriction- and recombination-defective.

An example of these is the strain DH5αMCR, which has been described by Grant et al. (Proceedings of the National Academy of Sciences USA, 87 (1990) 4645–4649) I.B.R. The long DNA fragments cloned with the aid of cosmids can then in turn be subcloned and subsequently sequenced in the usual vectors which are suitable for sequencing, such as is described e.g. by Sanger et al. (Proceedings of the National Academy of Sciences of the United States of America, 74:5463–5467, 1977) I.B.R.

The new DNA sequence of *C. glutamicum* which codes for the zwa1 gene and which is a constituent of the present invention as SEQ ID NO 1 was obtained in this manner. The amino acid sequence of the corresponding gene product of the zwa1 gene has furthermore been derived from the present DNA sequence. The resulting amino acid sequence of the zwa1 gene product is shown in SEQ ID NO 2.

Coding DNA sequences, which result from SEQ ID NO 1 by the degeneracy of the genetic code, are also a constituent of the invention. In the same way, DNA sequences which hybridize with SEQ ID NO 1 or parts of SEQ ID NO 1 are a constituent of the invention. Conservative amino acid exchanges, such as e.g. an exchange of glycine for alanine or of aspartic acid for glutamic acid in proteins, are furthermore known among experts as "sense mutations" which do not lead to a fundamental change in the activity of the protein, i.e. are of neutral function.

It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID NO 2 are also a constituent of the invention.

In the same way, DNA sequences which hybridize with SEQ ID NO 1 or parts of SEQ ID NO 1 are a constituent of the invention. Finally, DNA sequences which are prepared by the polymerase chain reaction (PCR) using primers which result from SEQ ID NO 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. Instructions for amplification of DNA sequences with the aid of the polymerase chain reaction (PCR) can be found by the expert, inter alia, in the handbook by Gait: Oligonukleotide synthesis: a practical approach (IRL Press, Oxford, UK, 1984) I.B.R. and in Newton and Graham: PCR (Spektrum Akademischer Verlag, Heidelberg, Germany, 1994) I.B.R.

The inventors have found that coryneform bacteria produce amino acids, in particular L-lysine, in an improved manner after over-expression of the zwa1 gene. To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production.

The expression is likewise improved by measures to prolong the life of the m-RNA. Furthermore, preventing the degradation of the enzyme protein also increases the enzyme activity. The genes or gene constructions can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in European Patent Specification EPS 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in Patent Application WO 96/15246 I.B.R., in Malumbres et al. (Gene 134, 15–24 (1993)) I.B.R., in Japanese Laid-Open Specification JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

By way of example, the zwa1 gene according to the invention was duplicated or over-expressed with the aid of the integration method such as is described e.g. in Reinscheid et al. (Applied and Environmental Microbiology 60, 126–132 (1994)) I.B.R. In this method, the complete gene is cloned in a plasmid vector, which can replicate in a host (typically $E.$ $coli$) but not in $C.$ $glutamicum$. Possible vectors are, for example, pSUP301 (Simon et al., Bio/Technology 1, 784–791 (1983)) I.B.R., pK18mob oder pK19mob (Schäfer et al., Gene 145, 69–73 (1994)) I.B.R., pGEM-T (Promega corporation, Madison, Wis., USA) I.B.R., pCR2.1-TOPO (Shuman (1994) I.B.R. Journal of Biological Chemistry 269:32678–84; U.S. Pat. No. 5,487,993) I.B.R., pCR®Blunt (Invitrogen, Groningen, Holland; Bernard et al., Journal of Molecular Biology, 234: 534–541 (1993)) I.B.R. or pEM1 (Schrumpf et al, 1991, Journal of Bacteriology 173:4510–4516) I.B.R. The plasmid vector, which contains the gene to be amplified, is then transferred into the desired strain of $C.$ $glutamicum$ by conjugation or transformation. The method of conjugation is described, for example, by Schäfer et al. (Applied and Environmental Microbiology 60, 756–759 (1994)) I.B.R.

Methods for transformation are described, for example, by Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a "cross over" event, the resulting strain contains two copies of the gene in question. The strain DSM5715::pCR2.1zwa1exp, which carries two copies of the zwa1 gene, was prepared in this manner with the aid of the integration plasmid pCR2.1zwa1exp.

In addition, it may be advantageous for the production of amino acids, in particular L-lysine, to amplify, in particular to over-express, one or more enzymes of the particular biosynthesis pathway of glycolysis, of anaplerosis, of the citric acid cycle or of amino acid export, in addition to the Zwa1 gene product.

It may thus be advantageous, for example for the preparation of L-lysine, for one or more of the genes chosen from the group consisting of the dapA gene which codes for dihydrodipicolinate synthase (EP-B 0 197 335) I.B.R., the lysC gene which codes for a feed back resistant aspartate kinase the dapD gene which codes for tetrahydrodipicolinate succinylase (Wehrmann et al., Journal of Bacteriology 180, 3159–3165 (1998)) I.B.R., the dapE gene which codes for succinyl diaminopimelate desuccinylase (Wehrmann et al., Journal of Bacteriology 177: 5991–5993 (1995)) I.B.R., the gap gene which codes for glyceraldehyde 3-phosphate dehydrogenase (Eikmanns (1992). Journal of Bacteriology 174:6076–6086) I.B.R., the pyc gene which codes for pyruvate carboxylase (Eikmanns (1992). Journal of Bacteriology 174:6076–6086) I.B.R., the mqo gene which codes for malate:quinone oxidoreductase (Molenaar et al., European Journal of Biochemistry 254, 395–403 (1998)) I.B.R., the lysE gene which codes for lysine export (DE-A-195 48 222) I.B.R.

to be over-expressed at the same time.

For the production of amino acids, in particular L-lysine, it may furthermore be advantageous to attenuate, in addition to the zwa1 gene, the gene which codes for phosphate pyruvate carboxykinase (DE 199 50 409.1; DSM 13047) I.B.R. and/or the pgi gene which codes for glucose 6-phosphate isomerase (U.S. Ser. No. 09/396,478; DSM 12969) I.B.R.

at the same time.

In addition to over-expression of the zwa1 gene it may furthermore be advantageous, for the production of amino acids, in particular L-lysine, to eliminate undesirable side reactions, (Nakayama: "Breeding of Amino Acid Producing Microorganisms", in: Overproduction of Microbial Products, Krumphanzl, Sikyta, Vanek (eds.), Academic Press, London, UK, 1982) I.B.R.

In addition to amplification of the zwa1 gene, it may be advantageous to attenuate the zwa2 gene or the action of the associated gene product of the zwa2 gene. The corresponding gene and the associated measures are to be found in Patent Application 199 59 327.2 I.B.R. filed in parallel.

An integration vector suitable for insertion mutagenesis, pCR2.1zwa2int, has been deposited under no. DSM13113 in E. coli TOP10F'.

Plasmid pCR2.1zwa2int comprises the plasmid pCR2.1-TOPO described by Mead et al. (Bio/Technology 9:657–663 (1991)) I.B.R., into which an internal fragment of the zwa2 gene, shown in SEQ-ID-No. 1 of German Patent Application 199 59 327.2 I.B.R., has been incorporated. After transformation and homologous recombination in the chromosomal zwa2 gene (insertion), this plasmid leads to a total loss of function. By way of example, the strain DSM5715::pCR2.1zwa2int, the Zwa2 gene product of which is eliminated, was prepared in this manner.

The microorganisms prepared according to the invention can be cultured continuously or discontinuously in the batch process (batch culture) or in the fed batch (feed process) or repeated fed batch process (repetitive feed process) for the purpose of production of amino acids, in particular L-lysine. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) I.B.R. or in the textbook by Storhas (Bioreaktoren und periphere Einrichtungen [Bioreactors and Peripheral Equipment] (Vieweg Verlag, Braunschweig/Wiesbaden, 1994)) I.B.R.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth.

Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids.

To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of lysine has formed. This target is usually reached within 10 hours to 160 hours.

The analysis of L-lysine can be carried out by anion exchange chromatography with subsequent ninhydrin derivatization, as described by Spackman et al. (Analytical Chemistry, 30, (1958), 1190) I.B.R. beschrieben.

The following microorganism has been deposited at the Deutsche Sammlung für Mikrorganismen und Zellkulturen (DSMZ=German Collection of Microorganisms and Cell Cultures, Braunschweig, Germany) in accordance with the Budapest Treaty: Escherichia coli strain Top10F'/pCR2.1zwa1exp as DSM 13115.

The process according to the invention is used for the fermentative preparation of amino acids, in particular L-lysine. In addition to amplification of the zwa1 gene, it may be advantageous to attenuate the zwa2 gene. The corresponding gene or the vector suitable for the insertion mutagenesis, pCR2.1zwa2int, is deposited in E.coli TOP10F' under number DSM13113.

EXAMPLES

The present invention is explained in more detail in the following with the aid of embodiment examples.

Example 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al., (1995, Plasmid 33:168–179) I.B.R. and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250).

The DNA of the cosmid vector SuperCos1 (Wahl et al. (1987) Proceedings of the National Academy of Sciences USA 84:2160–2164) I.B.R., obtained from the company Stratagene (La Jolla, USA, Product Description SuperCos1 Cosmid Vektor Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04).

The ligation mixture was then packed in phages with the aid of Gigapack II XL Packing Extracts (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) I.B.R. the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor) I.B.R., the cells being plated out on LB agar (Lennox, 1955, Virology, 1:190) I.B.R. with 100 μg/ml ampicillin. After incubation overnight at 37° C., recombinant individual clones were selected.

Example 2

Isolation and Sequencing of the Zwa1 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from the company Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor) I.B.R., the DNA mixture being incubated overnight with T4 ligase (Pharmacia Biotech, Freiburg, Germany).

This ligation mixture was then electroporated (Tauch et al. 1994, FEMS Microbiol Letters, 123:343-7) I.B.R. into the *E. coli* strain DH5αMCR (Grant, 1990, Proceedings of the National Academy of Sciences U.S.A., 87:4645–4649) I.B.R. and plated out on LB agar (Lennox, 1955, Virology, 1:190) with 50 μg/ml zeocin. The plasmid preparation of the recombinant clones was carried out with Biorobot 9600 (Product No. 900200, Qiagen, Hilden, Germany).

The sequencing was carried out by the dideoxy chain-stopping method of Sanger et al. (1977, Proceedings of the National Academy of Sciences U.S.A., 74:5463–5467) I.B.R. with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0 I.B.R. The individual sequences of the pZero1 derivatives were assembled to a continuous contig. The computer-assisted coding region analysis were prepared with the XNIP program (Staden, 1986, Nucleic Acids Research, 14:217–231) I.B.R. Further analyses were carried out with the "BLAST search program" (Altschul et al., 1997, Nucleic Acids Research, 25:3389–3402) I.B.R. against the non-redundant databank of the "National Center for Biotechnology Information" (NCBI, Bethesda, Md., USA) I.B.R.

The resulting nucleotide sequence of the zwa1 gene is shown in SEQ ID NO 1. Analysis of the nucleotide sequence showed an open reading frame of 597 base pairs, which was called the zwa1 gene. The zwa1 gene codes for a polypeptide of 199 amino acids, which is shown in SEQ ID NO 2.

Example 3

Preparation of a Vector for Over-Expression of Zwa1

From the strain ATCC 13032, chromosomal DNA was isolated by the method of Eikmanns et al. (Microbiology 140:1817–1828 (1994)) I.B.R. On the basis of the sequence of the zwa1 gene known for *C. glutamicum* from example 2, the following oligonucleotides were chosen for the polymerase chain reaction:

```
zwa1-d1:
5' TCA CA CCG ATG ATT CAG GC 3'
SEQ ID NO:3 zwa1-d2:
5' AGA TTT AGC CGA CGA AAG CG 3'
SEQ ID NO:4
```

The primers shown were synthesized by MWG Biotech (Ebersberg, Germany) and the PCR reaction was carried out by the standard PCR method of Innis et al. (PCR protocols. A guide to methods and applications, 1990, Academic Press)

with Pwo-Polymerase from Boehringer. With the aid of the polymerase chain reaction, a DNA fragment approx. 1.0 kb in size was isolated, this carrying the zwa1 gene.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663) I.B.R. The E. coli strain Top10F' was then electroporated with the ligation batch (Hanahan, In: DNA cloning. A practical approach. Vol. I. IRL-Press, Oxford, Washington D.C., USA) I.B.R. Selection for plasmid-carrying cells was made by plating out the transformation batch on LB agar (Sambrook et al., Molecular cloning: a laboratory manual. $2^{nd}$ Ed. Cold Spring Harbor Laboratory Press, Cold Spring Harbor, N.Y.) I.B.R., which had been supplemented with 25 mg/l kanamycin.

Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1zwa1exp.

Example 4

Duplication of the Zwa1 Gene in the Lysine Producer DSM 5715

The vector pCR2.1zwa1exp mentioned in example 6 was electroporated by the electroporation method of Tauch et al. (FEMS Microbiological Letters, 123:343–347 (1994)) I.B.R. in Corynebacterium glutamicum DSM 5715. Strain DSM 5715 is an AEC(aminoethylcysteine)-resistant lysine producer. The vector pCR2.1zwa1exp cannot replicate independently in DSM 5715 and is retained in the cell only if it has integrated into the chromosome of DSM 5715.

Selection of clones with pCR2.1zwa1exp integrated into the chromosome was carried out by plating out the electroporation batch on LB agar (Sambrook et al., Molecular cloning: a laboratory manual. $2^{nd}$ Ed. Cold Spring Harbor Laboratory Press, Cold Spring Harbor, N.Y., 1989) I.B.R., which had been supplemented with 15 mg/l kanamycin. For detection of the integration, control PCR reactions were carried out by the standard method of Innis et al. (PCR protocols. A guide to methods and applications, 1990, Academic Press) I.B.R. with Pwo-Polymerase from Boehringer. By combination of the primers zwa1-d1 and zwa1-d2 (cf. example 3) with the primers M13 universal forward (5'-gttttcccagtcacgac-3') (Invitrogen Corporation, Cat. No. N540-02) and M13 universal reverse (5'-caggaaacagctatgac-3') (Invitrogen Corporation, Cat. No. N530-02), which can bind only within the sequence of the vector pCR2.1zwa1exp, it could be demonstrated that the plasmid pCR2.1zwa1exp had been inserted into the chromosome of the lysine producer DSM5715. The strain was called DSM5715::pCR2.1zwa1exp.

Example 5

Preparation of Lysine

The C. glutamicum strain DSM5715::pCR2.1zwa1exp obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l) for 24 hours at 33° C. Starting from this agar plate culture, a preculture was seeded (10 ml medium in a 100 ml conical flask). The complete medium CgIII was used as the medium for the preculture. Kanamycin (25 mg/l) was added to this. The preculture was incubated for 48 hours at 33° C. at 240 rpm on a shaking machine. A main culture was seeded from this preculture such that the initial OD (660 nm) of the main culture was 0.1. Medium MM was used for the main culture.

| Medium MM | |
|---|---|
| CSL (corn steep liquor) | 5 g/l |
| MOPS | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). Ion exchange chromatography and post-column derivatization with ninhydrin detection determined the amount of lysine formed with an amino acid analyzer from Eppendorf-BioTronik (Hamburg, Germany)

The result of the experiment is shown in table 1.

TABLE 1

| Strain | OD (660) | Lysine HCl g/l |
|---|---|---|
| DSM5715::pCR2.1zwa1exp | 12.1 | 11.93 |
| DSM5715 | 13.1 | 9.54 |

The abbreviations and designations used have the following meaning.

| | |
|---|---|
| ColE1 ori: | Replication origin of the plasmid ColE1 |
| lacZ: | 5' end of the β-galactosidase gene |
| f1 ori: | Replication origin of phage f1 |
| KmR: | Kanamycin resistance |
| ApR: | Ampicillin resistance |
| EcoRI: | Cleavage site of the restriction enzyme EcoRI |
| zwa1 | zwa1 gene |

Further variations and modifications of the present invention will be apparent to those skilled in the art from a reading of the foregoing and are encompassed by the claims appended hereto.

German patent application 199 59 328.0 I.B.R. is relied upon and incorporated herein by reference.

We claim:

1. An isolated polynucleotide consisting of a polynucleotide sequence which encodes the protein of SEQ ID NO:2.

2. The isolated polynucleotide of claim 1, wherein said polynucleotide is isolated from the genus *Corynebacterium*.

3. The isolated polynucleotide of claim 1, wherein said polynucleotide is isolated from the species *Corynebacterium glutamicum*.

4. A vector comprising the isolated polynucleotide of any one of claims 1 to 3.

5. A An isolated host cell transformed with the isolated polynucleotide of any one of claims 1 to 3.

6. An isolated polynucleotide, comprising nucleotides 413 to 1009 of SEQ ID NO:1 or a degenerate variant thereof.

7. An isolated polynucleotide, comprising a full complement of the polynucleotide of claim 6.

8. An isolated polynucleotide comprising SEQ ID NO:1.

9. An isolated polynucleotide, comprising a full complement of the polynucleotide of claim 8.

10. An isolated polynucleotide consisting of SEQ ID NO:1 or a fragment thereof wherein said fragment encodes a protein consisting of the amino acid sequence of SEQ ID NO:2.

11. An isolated polynucleotide fragment of SEQ ID NO:1 consisting of at least 30 consecutive nucleotides of SEQ ID NO:1.

12. A vector comprising the isolated polynucleotide of any one of claims 6 to 10.

13. An isolated host cell transformed with the isolated polynucleotide of any one of claims 6 to 10.

14. *Escherichia coli* DSM 13115.

15. A coryneform bacterium serving as a host cell transformed with a vector comprising the isolated polynucleotide of claim 1.

16. A coryneform bacterium serving as a host cell transformed with a vector comprising the isolated polynucleotide of claim 6.

17. A coryneform bacterium serving as a host cell transformed with a vector comprising the isolated polynucleotide of SEQ ID NO:1.

18. An isolated polynucleotide, comprising a full complement of SEQ ID NO:1.

* * * * *